US011883368B2

(12) United States Patent
Strand et al.

(10) Patent No.: US 11,883,368 B2
(45) Date of Patent: *Jan. 30, 2024

(54) LEAVE-ON ORAL CARE COMPOSITIONS

(71) Applicant: The Procter & Gamble Company, Cincinnati, OH (US)

(72) Inventors: Ross Strand, Singapore (SG); Yang Su, Beijing (CN); Yunming Shi, Beijing (CN); Xiaoxiao Li, Beijing (CN); Guannan Wang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 595 days.

This patent is subject to a terminal disclaimer.

(21) Appl. No.: 16/899,919

(22) Filed: Jun. 12, 2020

(65) Prior Publication Data
US 2020/0390801 A1 Dec. 17, 2020

(30) Foreign Application Priority Data

Jun. 14, 2019 (WO) ................ PCT/CN2019/091325
Jun. 11, 2020 (WO) ................ PCT/CN2020/095578

(51) Int. Cl.
| | | |
|---|---|---|
| *A61K 31/728* | (2006.01) | |
| *A61K 31/375* | (2006.01) | |
| *A61K 31/355* | (2006.01) | |
| *A61K 31/197* | (2006.01) | |
| *A61C 19/06* | (2006.01) | |
| *A61K 31/7016* | (2006.01) | |
| *A61K 9/00* | (2006.01) | |
| *A61K 8/73* | (2006.01) | |
| *A61K 8/81* | (2006.01) | |
| *A61K 8/67* | (2006.01) | |
| *A61K 8/60* | (2006.01) | |
| *A61Q 11/00* | (2006.01) | |
| *A61K 47/32* | (2006.01) | |

(52) U.S. Cl.
CPC .......... *A61K 31/728* (2013.01); *A61C 19/063* (2013.01); *A61K 8/60* (2013.01); *A61K 8/673* (2013.01); *A61K 8/676* (2013.01); *A61K 8/678* (2013.01); *A61K 8/735* (2013.01); *A61K 8/8147* (2013.01); *A61K 9/0053* (2013.01); *A61K 31/197* (2013.01); *A61K 31/355* (2013.01); *A61K 31/375* (2013.01); *A61K 31/7016* (2013.01); *A61K 47/32* (2013.01); *A61Q 11/00* (2013.01); *A61K 2800/00* (2013.01); *A61K 2800/30* (2013.01)

(58) Field of Classification Search
None
See application file for complete search history.

(56) References Cited

U.S. PATENT DOCUMENTS

| | | |
|---|---|---|
| 5,876,744 A | 3/1999 | Della et al. |
| 9,532,939 B2 | 1/2017 | Ripley et al. |
| 10,383,796 B2 | 8/2019 | Truitt |
| 2002/0028241 A1 | 3/2002 | Foreman et al. |
| 2005/0142076 A1 | 6/2005 | Fukunaga et al. |
| 2007/0003502 A1 | 1/2007 | Tanabe et al. |
| 2007/0237726 A1 | 10/2007 | White et al. |
| 2009/0068122 A1 | 3/2009 | Pilch |
| 2011/0104081 A1 | 5/2011 | Scott |
| 2012/0014883 A1 | 1/2012 | Scott |
| 2012/0082630 A1 | 4/2012 | Haught |
| 2012/0202767 A1 | 8/2012 | Di |
| 2014/0242005 A1 | 8/2014 | Koumans |
| 2018/0333349 A1 | 11/2018 | Ansari et al. |
| 2019/0021966 A1 | 1/2019 | Jha et al. |
| 2020/0054667 A1 | 2/2020 | Mevorat Kaplan et al. |
| 2020/0390676 A1 | 12/2020 | Strand |
| 2020/0390677 A1 | 12/2020 | Strand |

FOREIGN PATENT DOCUMENTS

| | | |
|---|---|---|
| CN | 101415731 A | 4/2009 |
| CN | 102125507 A | 7/2011 |
| CN | 105213298 A | 1/2016 |
| CN | 105434315 A | 3/2016 |
| CN | 106963727 A | 7/2017 |
| CN | 107432853 A | 12/2017 |
| CN | 107468553 A | 12/2017 |
| CN | 107496195 A | 12/2017 |
| CN | 107536725 A | 1/2018 |
| CN | 108888770 A | 11/2018 |
| CN | 108939079 A | 12/2018 |
| CN | 109010471 A | 12/2018 |
| CN | 109528805 A | 3/2019 |
| CN | 109820821 A | 5/2019 |
| CN | 110123702 A | 8/2019 |
| DE | 102017005168 A1 | 12/2018 |
| EP | 2666517 A1 | 11/2013 |
| EP | 3056195 A1 | 8/2016 |
| JP | H08500578 A | 1/1996 |

(Continued)

OTHER PUBLICATIONS

PCT Suppl. Search Report and Written Opinion for PCT/CN2020/095578 dated Sep. 7, 2021, 11 pages.
International Search Report and Written Opinion; Application Ser. No. PCT/CN2019/091325, dated Mar. 12, 2020, 9 pages.
International Search Report and Written Opinion; Application Ser. No. PCT/CN2020/095578, dated Sep. 7, 2020, 9 pages.
All Office Actions; U.S. Appl. No. 16/899,834.
All Office Actions; U.S. Appl. No. 16/899,882.

(Continued)

Primary Examiner — Celeste A Roney
(74) Attorney, Agent, or Firm — Elizabeth A. Conklin

(57) ABSTRACT

Leave-on oral care compositions comprising a hyaluronic acid, and a gum-strengthening polyol are provided for promoting Gum Health of a user.

20 Claims, No Drawings

(56) References Cited

FOREIGN PATENT DOCUMENTS

| | | | | |
|---|---|---|---|---|
| JP | 2002029950 | A | 1/2002 | |
| JP | 2004012747 | A1 | 1/2004 | |
| JP | 2009274967 | A | 11/2009 | |
| JP | 2010511053 | A | 4/2010 | |
| JP | 2010138080 | A | 6/2010 | |
| JP | 2012153677 | A | 8/2012 | |
| JP | 2014501733 | A | 1/2014 | |
| JP | 2015189708 | A | 11/2015 | |
| JP | 2017523993 | A | 8/2017 | |
| JP | 2018002719 | A | 1/2018 | |
| JP | 6519930 | B2 * | 5/2019 | ............... A23L 5/00 |
| KR | 100794264 | B1 | 1/2008 | |
| KR | 100805635 | B1 | 2/2008 | |
| WO | 2016112998 | A1 | 7/2016 | |
| WO | 2018212771 | A1 | 11/2018 | |
| WO | 2019025599 | A1 | 2/2019 | |

OTHER PUBLICATIONS

Database GNPD [Online] MINTEL; Anonymous: "Gengigel Oral Hygiene Range", XP055809999, Database accession No. 341172, Feb. 17, 2005.

Database GNPD [Online] MINTEL; Anonymous: "Travel Kit", XP055729622, Database accession No. 6318883, Feb. 12, 2019.

Dahiya P, Kamal R. Hyaluronic acid: A boon in periodontal therapy. North Am J Med Sci 2013;5:309-15. (Year: 2013).

All Office Actions; U.S. Appl. No. 16/899,834, dated Oct. 4, 1021.

All Office Actions; U.S. Appl. No. 16/899,882, dated Jul. 6, 2021.

Google patent search hyaluronic polyacrylic water, Retrieved from: https://patents.google.com/?q=hyaluronic+polyacrylic+water&oq=hyaluronic+polyacrylic+water, Retrieved on Jun. 29, 2021, 2 Pages.

Google scholar search hyaluronic polyacrylic mucoadhesive, Retrieved from: https://scholar.google.com/scholar?hl=en&as_sdt=0%2C5&q=hyaluronic+polyacrylic+mucoadhesive&btnG=, Retrieved on Jun. 29, 2021, 2 Pages.

Google search hyaluronic polyacrylic mucoadhesive, Retrieved from: https://www.google.com/search?q=hyaluronic_polyacrylic_mucoadhesive&rlz=1C1GCEA_enIN879IN879&oq=hyaluronic_polyacrylic_mucoadhesive&aqs=chrome..69i57.1423j0j15&sourceid=chrome&ie=UTF-8, Retrieved on Jun. 29, 2021, 2 Pages.

Google search polyvinylpyrrolidone mucoadhesive properties hyaluronic acid polyacrylic, Retrieved from: https://www.google.com/search?q=polyvinylpyrrolidone+mucoadhesive+properties+hyaluronic+acid+polyacrylic&rlz=1C1GCEA_enIN879IN879&oq=polyvinylpyrrolidone+mucoadhesive+properties+hyaluronic+acid+polyacrylic&aqs=chrome..69i57.505j0j15&sourceid=chrome&ie=UTF-8, Retrieved on Jun. 29, 2021, 2 Pages.

Roy et al., Polymers in Mucoadhesive Drug-Delivery Systems: A Brief Note, Designed monomers and polymers, vol. 12, Issue 6, Jan. 1, 2009, pp. 483-495.

U.S. Appl. No. 16/899,834, To Be Assigned, filed Jun. 12, 2020, Ross (NMN) Strand et al.

U.S. Appl. No. 16/899,882, To Be Assigned, filed Jun. 12, 2020, Ross (NMN) Strand et al.

* cited by examiner

LEAVE-ON ORAL CARE COMPOSITIONS

FIELD OF THE INVENTION

The present invention relates to a leave-on oral care composition for promoting Gum Health of a user. In particular, such oral care compositions comprising a hyaluronic acid and a gum-strengthening polyol are useful for providing improved barrier function/protection and sensory experience for the user.

BACKGROUND OF THE INVENTION

Gum disease, such as gingivitis and/or periodontitis, gives rise to acute and chronic gum inflammation in the oral cavity. "Gingivitis" is the milder form of the disease. Symptoms of gingivitis may include: gingival bleeding; and redness, swollen, or tender gums. If left untreated, gingivitis can advance to "periodontitis". With periodontitis, gums pull away from the teeth and form spaces called "periodontal pockets" that can become infected by pathogenic bacteria. The bacteria are present on the tooth root surfaces as biofilms. The bacteria in the biofilms can attack the gingival and underlying alveolar bone supporting teeth. These attacks can cause major damage to the soft tissue and bone that support teeth. In the later stage of gum disease (i.e., "advanced periodontitis"), more serious problems of loosening of teeth and eventual tooth loss can occur.

Users having gum problems have typically been limited to brushing teeth with antibacterial toothpastes as a solution at home. This mechanism can help clean and control the plaque and bacteria and associated toxin challenge on the host. However, due to the limited residence time of brushing, 2 minutes, there is little time to repair, or even strengthen the host tissue. Accordingly, users expect a regimen that can be applied to the host tissue for a longer time and to repair, strengthen and rejuvenate the gum. In order to meet such users' expectation, a number of gel or ointment products that can be applied to the oral cavity have been developed to provide such benefits. For example, a user can apply a gel formulation product onto oral tissue, e.g. gum area and leave for some time before expectorating or alternatively without expectorating or rinsing off. Desirable products require sufficient substantivity and viscosity to enable application to the oral cavity, to adhere to the oral tissue and to release the contained oral care benefits agents over an extended period of time. Desirable products are also required to provide improved Gum Health benefit to users (e.g., barrier function/protection or gingival wound heading benefits).

Therefore there is a continuous need to provide a leave-on composition which not only has a good spreadability and/or adhesion to provide good sensory benefits to users, but also provides desirable Gum Health benefits (e.g., barrier protection benefits or gingival wound healing, etc.) to users.

SUMMARY OF THE INVENTION

A novel technology for formulating a leave-on oral care composition is developed by the inventors to meet at least some of the needs described above. Particularly, it is a surprising discovery that a leave-on oral care composition comprising hyaluronic acid and a gum-strengthening polyol provides improved Gum Health benefits to the users, especially good barrier function/protection benefit. Meanwhile, such oral care composition described herein provides users with a desirable sensory feel.

It is advantageous that the leave-on oral care composition containing a hyaluronic acid and a gum-strengthening polyol can provide the users an improved Gum Health benefit, such as gum barrier protection benefit.

Without being bound by any theory, it is believed that the leave-on oral care composition of the present invention, which exhibits improved wound healing benefit and barrier function benefit, may in turn help to relieve gingival pain, promote gingival regeneration, accelerate repairing of mucosal/gingival damage and healing of gingival bleeding wound, and/or enhancing gingival immunity/resistance. The leave-on oral care composition may further help forming a protective film over lesion and irritation caused by ill-fitting dentures. The leave-on oral care composition may further help repairing or healing of gingival damage post root scaling/planning or gum grafts. The leave-on oral care composition may even further to help improve hydration to the mucosal and even help alleviate or relieve dry mouth.

It is also advantageous that the leave-on oral care composition has an optimal viscosity profile so to provide a good spreadability.

It is still advantageous that the leave-on oral care composition is not heavy, overly sticky/tacky and provide users enjoyable experiences, such as refreshing, safe, and effective feel.

It is further advantageous to provide users a pleasant mouth feel and taste for long term use, which is recognized as a balancing act between substantivity, adhesiveness and viscosity.

It is yet advantageous to apply the leave-on oral care composition after brushing teeth, or as the last step of oral hygiene regimen. It is advantageous that the leave-on oral care composition is applied on the soft tissue of the oral cavity, leaving for more than 2 minutes, preferably more than 10 minutes, and without being rinsed off or expectorated.

It is further advantageous to apply the leave-on oral care composition to the gum by a delivery carrier, wherein the delivery carrier may comprise strip, film of material, dental tray, aligner, sponge material, applicator, or mixtures thereof.

In one aspect, the present invention is directed to an oral care composition comprising a) from 30% to 85%, by weight of the composition, of total water content; b) from about 0.01% to about 10%, by weight of the composition, of a hyaluronic acid or a salt thereof; c) from about 0.1% to about 20%, by weight of the composition, of a gum-strengthening polyol. Preferably, the oral care composition is substantially free of abrasives. Preferably, the oral care composition is a leave-on composition. Preferably, the gum-strengthening polyol is selected from the group consisting of trehalose, rafiose, stachyose, verbascose, isomalt, maltitol, lactitol, maltotriitol, maltotetraitol, polyglycitol, and combinations thereof. Preferably, the gum-strengthening polyol is present in the amount of about 0.5% to about 18%, preferably from about 1% to about 15%, by weight of the composition.

In another aspect, the present invention is directed to an oral care composition comprising a) from about 0.2% to about 2%, by weight of the composition, of a hyaluronic acid or a salt thereof; b) from about 0.5% to about 5%, by weight of the composition, of polyacrylic acid; c) from about 0.5% to about 5%, by weight of the composition, of an additional; d) from about 0.5% to about 15%, by weight of the composition, of trehalose; and d) from about 30% to about 75%, by weight of the composition, of a total water content; wherein the oral care composition is substantially free of abrasives; and wherein the oral care composition is a leave-on composition in a gel form.

In still another aspect of the present invention, there is provided a method of improving Gum Health of a subject using the oral care composition as defined therein, comprising the step of applying the oral care composition onto the intraoral tissue of the subject, on which the oral care composition is left without removal for a duration of time from 1 minute to 1000 minutes, preferably from 2 minutes to 200 minutes; optionally the applying step can be conducted as the last step of an oral hygiene regimen.

In still another aspect of the present invention, there is provided a method of improving Gum Health of a subject, comprising at least two steps: (a) brushing teeth with a toothpaste, preferably an antibacterial toothpaste, more preferably a stannous-containing toothpaste, and even more preferably a toothpaste containing a stannous ion source and an amino acid; and subsequently, preferably immediately followed by (b) applying the oral are composition as defined herein onto the intraoral tissue of the subject, preferably applying along the gingival margin, sulcus or pockets, on which the oral care composition is left without removal for a duration of time from 1 minute to 1000 minutes.

In yet still another aspect of the present invention, there is provided a kit comprising an oral care composition of the present invention and a delivery carrier, wherein the delivery carrier comprises strip, film of material, dental tray, aligner, sponge material, applicator, or mixtures thereof. In a preferred example, the kit comprises an oral care composition of the present invention and an applicator having a handle and a head. There is also provided a kit comprising a toothpaste and the oral care composition of the present invention. In a preferred example, the kit comprises an antibacterial toothpaste and the oral care composition of the present invention, where the toothpaste is preferably a stannous-containing toothpaste, more preferably is a toothpaste comprising a stannous ion source and an amino acid. Preferably, the toothpaste and the oral care composition are separately and sequentially applied to improve Gum Health.

These and other features of the present invention will become apparent to one skilled in the art upon review of the following detailed description when taken in conjunction with the appended claims.

DETAILED DESCRIPTION OF THE INVENTION

Definitions

As used herein, the articles including "a" and "an" when used in a claim, are understood to mean one or more of what is claimed or described.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "gingival gel" or "gum gel" as used herein means a product or a composition is in a form of gel which intent to primarily applied to the gum of a subject, preferably more than 50% of the product or composition is applied to the gum.

As used herein, "leave-on" means a product or a composition is adopted or applied onto a surface for a certain amount of time, e.g. more than one minute, preferably more than two minutes. Preferably, a "leave-on" gel means a gel product or composition which is intent not to be rinsed off or to be expectorated.

The term "Gum Care" means those benefits aiming to alleviate one or more symptoms of the earlier stage of gum disease (i.e., gingivitis), which includes: relief of red, swollen, or tender gums; and/or stem gum bleeding.

The term "Gum Health" as used herein refers to inherent or promoted benefits of an oral care composition to provide "Gum Care" benefits that include at least improve gingival wound healing, as well as, providing additional improve reduction of bacterial activity to mitigate the harmful effects of bacteria as it relates to gum disease, including gingivitis, periodontitis or both.

The term "promoting" as used herein means to promote and/or enhance the Gum Health benefits associated with using the oral care compositions of the present invention in the oral cavity.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

The term "oral hygiene regimen" or "regimen" means the use of two or more separate and distinct treatment steps for oral health. e.g. toothpaste, mouth rinse, floss, toothpicks, spray, water irrigator, massager.

The term "total water content" as used herein means both free water and water that is bound by other ingredients in the oral care composition.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

All measurements referred to herein are made at 25° C. (i.e., room temperature) unless otherwise specified.

Oral Care Compositions

The oral care composition described in the present invention is configured for applying on the gingival tissue, as well as other soft tissue (e.g. buccal mucosa) inside the oral cavity of a subject. It has been surprisingly discovered that an oral care composition having both an optimal viscosity and a good adhesion and retention efficacy provides a better sensory benefit to the users, and also is particularly useful for promoting Gum Health benefits to users.

The oral care composition described therein is a leave-on composition. The leave-on composition is applied to the gingival tissue, e.g. gumline area, and left on for more than 2 minutes, preferably more than 10 minutes. In some examples, the composition is applied to the gingival tissue and left on for more than 15 minutes, or more than 30 minutes, or even more than 60 minutes or longer. Preferably, the composition of the present invention is applied on the gingival tissue without rinsing off. Preferably, the leave-on composition is applied to the gingival tissue as the last step of oral hygiene regimen. For example, the leave-on composition of the present invention is applied after brushing teeth, and optionally after using mouth rinse and/or floss.

In one aspect, the present invention is directed to an oral care composition which is in a gel form. It is desirable to have a gel for use in the present invention that enables easy application, thin layer formation and evenly spread into gingival sulcus/pockets and along gingival gum line. The oral care composition has a Viscosity Consistency Coefficient K of about 50 Pa·s to about 250 Pa·s, as measured by the Rheological Test Method described herein. Preferably, the oral care composition has a Viscosity Consistency Coefficient K of about 50 Pa·s to about 200 Pa·s, preferably from about 50 Pa·s to about 150 Pa·s, more preferably from about 50 Pa·s to about 120 Pa·s. This optimal viscosity profile range provides better sensory experience of spreadability for a user. If a product is too viscous, it would be hard for a user to spread it evenly onto gingival tissue. If the product has a too low viscosity, it is runny and hard to be retained on appropriate area by finger or applicator.

In one aspect, the oral care composition of present invention has a desirable mucoadhesion property. Mucoadhesion can be defined as adhesive interaction between two surfaces where one is at least mucosa for a given period through interfacial forces with a consequent decreased in the surface energy. Mucoadhesion polymers for oral care application should ideally (1) easily retain hydrophilic and lipophilic active ingredients and not hinder their release; (2) promote active ingredient penetration and absorption, (3) adhere as quickly as possible to biological substrate and be retained for a period of time, (4) be safe, (5) be cost effective and (6) provide users acceptable application.

The oral care composition of present invention has a Mucoadhesion Index in the range of not less than about 0.6 FI %, as measured by the Mucoadhesion Test Method described herein. Preferably, the oral care composition has a Mucoadhesion Index of no less than about 0.8 FI %, more preferably no less than about 1.0 FI %. For instance, the oral care composition may have a Mucoadhesion Index of no less than about 1.2 FI %, or no less than about 1.3 FI %, or no less than about 1.5 FI %, or no less than about 1.8 FI %, or no less than about 2.0 FI %. Preferably, the oral care composition has a Mucoadhesion Index of less than about 20 FI %, preferably less than about 15 FI %, more preferably less than about 10 FI %.

Hyaluronic Acid and Salts

The oral care composition of the present invention comprises a hyaluronic acid or a salt thereof. Hyaluronic acid is a polysaccharide present in the connective tissue of vertebrates, a polymer of glucuronic acid and n-acetyglucosylamine, and is a member of glucosamine family with a high molecular weight Mw. Hyaluronic acid (Hyaluronan) is an indispensable component of intact, healthy gingiva, and oral mucosal tissue. It has many properties that make it a potentially ideal molecule for assisting wound healing by inducing early granulation tissue formation, inhibiting inflammation, promoting epithelial turnover and also connective tissue angiogenesis. Preferably, the hyaluronic acid used in the present invention has a weight average molecular weight (M.W) of from about 900,000 Daltons to about 5,000,000 Daltons, preferably from about 900,000 Daltons to about 3,000,000 Daltons; more preferably from about 900,000 Daltons to about 2,000,000 Daltons. The molecular weight of the hyaluronic acid can be measured using Gel Electrophoresis method. The hyaluronic acid of the present invention is present in the amount of from 0.01% to 5.0% by weight of the composition. Preferably, the hyaluronic acid is present in the amount of from 0.1% to 2%, more preferably from 0.2% to 0.8%, by weight of the composition. For example, the hyaluronic acid is present in the amount of about 0.2%, or about 0.3%, or about 0.4%, or about 0.5%, or about 0.6%, or about 0.7%, or about 0.8%, or about 0.9%, or about 1.0%, by weight of the composition. Any salt of the hyaluronic acid suitable for oral care product can be used in the present invention. Preferably, the hyaluronate salt may be sodium hyaluronate.

Gum-Strengthening Polyol

The oral care composition of the present invention comprises a gum-strengthening polyol. The applicant has discovered that gum-strengthening polyols have been shown to additionally strengthen the barrier function of epithelial cells in the oral cavity.

The term "gum-strengthening polyol" can be a sugar alcohol, a disaccharide, a polysaccharide, and preferably a non-reducing sugar. Sugar alcohols are a class of polyols that can be obtained through the hydrogenation of sugar compounds with the formula $(CHOH)_nH_2$, where n is seven or more, such as isomalt, maltitol, lactitol, maltotriitol, maltotetraitol, polyglycitol, or combinations thereof. Preferably, n is from about 7 to about 12. Even more preferably, the gum-strengthening polyol is isomalt, maltitol, lactitol, or combinations thereof.

Non-reducing sugars are a class of saccharides that do not generate any compounds containing an aldehyde or ketone functional group. Non-reducing sugars are stable in water and do not react with weak oxidizing agents to produce sugar alcohols. Non-reducing sugars cannot donate electrons to other molecules, and is typically a di, tri, terta, penta saccharide, such as sucrose, trehalose, raffinose, stachyose, verbascose, or combinations thereof. Preferably, the gum-strengthening polyol is trehalose. The gum barrier properties can be obtained from a combination mixture of polyols whereby all have seven or more hydroxyl functional groups.

The oral care composition can comprise from about 0.025% to about 20%, from about 0.1% to about 18%, from about 0.2% to about 15%, from about 0.5% to about 15%, or from about 1% to about 12%, by weight of the oral care composition, of a gum-strengthening polyol.

The gum-strengthening property can be characterized by Barrier Protection ability as described hereinbelow. For example, a polyol exhibiting the Barrier Protection of more than 10% at concentration of 0.5 wt % can be qualified as a gum-strengthening polyol. In other examples, the gum-strengthening polyol can include polyols having five or more hydroxyl functional groups as long which can provide above-mentioned Barrier Protection ability.

Mucoadhesive Polymer

The oral care composition of the present invention comprises polyacrylic acid as a mucoadhesive polymer. Polyacrylic acid (PAA) polymer is a generic term for the synthetic high molecular weight polymers of acrylic acid. These may be homopolymers of acrylic acid, crosslinked with an allyl ether pentaerythritol, allyl ether of sucrose or allyl ether of propylene. And, in a water solution at neutral pH, PAA is an anionic polymer, i.e. many of the side chains of PAA will lose their protons and acquire a negative charge. This makes PAAs polyelectrolytes, with the ability to absorb and retain water and swell to many times their original volume. Polyacrylic acid is also called carbomer as tradename. For example, Carbopol®-type polymers, such as Carbopol®, Pemulen® and Noveon®, are polymers of acrylic acid, crosslinked with polyalkenyl ethers or divinyl glycol. Carbomer commercial codes, e.g. 940™, indicate the molecular weight and the specific components of the polymer.

Preferably, the polyacrylic acid used in the invention is present in the amount of about 0.1% to about 10% by weight of the oral care composition. For example, the polyacrylic acid is present in the amount of from about 0.2% to about 5%, or from about 0.5% to about 8%, or from about 1.0% to about 5%, by weight of the oral care composition.

Additional Polymer

The oral care composition of the present invention may comprise an additional polymer. Preferably the oral care composition comprises from about 0.1% to about 10%, preferably from about 0.5% to about 6%, more preferably from about 1% to about 5%, yet still more preferably from about 1.3% to about 2.6%, by weight of the composition, of the additional polymer. The additional polymer is selected from natural gum, linear sulfated polysaccharide, anionic cellulose, nonionic cellulose derivative, polyvinyl pyrrolidine, polymers comprising at least a polycarboxylated ethylene backbone, and combinations thereof.

Preferably, a natural gum is selected from the group consisting of gum karaya, gum arabic (also known as acacia gum), gum tragacanth, xanthan gum, and combination thereof. More preferably, the natural gum is xanthan gum. Xanthan gum is a polysaccharide secreted by the bacterium *Xanthomonas camestris*. Generally, xanthan gum is composed of a penta-saccharide repeat units, comprising glucose, mannose, and glucuronic acid in a molar ratio of 2:2:1, respectively. The chemical formula (of the monomer) is $C_{35}H_{49}O_{29}$. In one example, the xanthan gum is from CP Kelco Inc (Okmulgee, US).

Preferably, the linear sulfated polysaccharide is a carrageenan. Examples of carrageenan include Kappa-carrageenan, Iota-carrageenan, Lambda-carrageenan, and combinations thereof. In one example, the linear sulfated polysaccharide is Iota-carrageenan.

Preferably, the anionic cellulose is a carboxymethyl cellulose ("CMC"). In one example, the CMC is prepared from cellulose by treatment with alkali and monochloroacetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A).

Preferably, the nonionic cellulose or derivative thereof has a weight average molecular weight range of 50,000 Daltons to 1,300,000 Daltons, and preferably an average degree of polymerization from 300 to 4,800. More preferably, the nonionic cellulose or derivative thereof is hydroxyethyl cellulose ("HEC"). In other examples, the nonionic cellulose may be hydroxypropyl cellulose or hydroxymethyl cellulose.

Preferably, the polymer comprising at least a polycarboxylated ethylene backbone is selected from the group consisting of: co-polymers of maleic anhydride with methyl vinyl ether having a weight average molecular weight of 30,000 Daltons to 1,000,000 Daltons; and co-polymers of maleic acid and acrylic acid or methacrylic.

In an example, the GANTREZ™ series of polymers are co-polymers of maleic anhydride with methyl vinyl ether having a weight average molecular weight (M.W.) of 30,000 Daltons to 1,000,000 Daltons. These co-polymers are available for example as GANTREZ™ AN139 (M.W. 500,000 Daltons), AN119 (M.W. 250,000 Daltons) and S-97 Pharmaceutical Grade (M.W. 70,000 Daltons), from Ashland Chemicals (Kentucky, USA).

In another example, the ACUSOL™ and the SOKALAN series of polymers include homopolymers of acrylic acid and copolymers of maleic acid and acrylic acid or methacrylic. Examples are 0:1000 to 1000:0 copolymers of maleic acid with acrylic acid having a weight average molecular weight (M.W.) of about 2,000 to about 1,000,000. These copolymers are commercially available as ACUSOL™ 445 and 445N, ACUSOL™ 531, ACUSOL™ 463, ACUSOL™ 448, ACUSOL™ 460, ACUSOL™ 465, ACUSOL™ 497, ACUSOL™ 490 from Dow Chemicals (Michigan, USA) and as Sokalan® CP 5, Sokalan® CP 7, Sokalan® CP 45, and Sokalan® CP 12 S from BASF (New Jersey, USA).

In some examples, the ratio of the mucoadhesive polymer and the additional polymer in the oral care composition of the present invention is from about 5:1 to about 1:5, preferably from about 3:1 to about 1:3. For example, the ratio of the polyacrylic acid and the additional polymer in the present oral care composition, by weight, is about 4:1, or about 3:1, or about 2:1, or about 1.5:1, or about 1:1, or about 1:1.5, or about 1:2, or about 1:2.5, or about 1:3, or about 1:4, or about 1:5.

Water

The term "orally acceptable carrier" as used herein means a liquid or semi-solid vehicle such as a paste or a gel for containing the active ingredients of the present invention and delivering them to the oral cavity. Water is commonly used as a carrier material in oral compositions due to its many benefits. For example, water is useful as a processing aid, is benign to the oral cavity and assists in quick foaming of toothpastes. Water may be added as an ingredient in its own or it may be present as a carrier in other common raw materials such as, for example, sorbitol and sodium lauryl sulphate. The term total water content as used herein means the total amount of water present in the oral care composition, whether added separately or as a solvent or carrier for other raw materials but excluding that which may be present as water of crystallization in certain inorganic salts.

The oral care composition of the present invention comprises at least about 30% of a total water content. Preferably, the oral care composition comprises from more than about 35% to about 85% of a total water content. In other embodiments, the compositions include from about 40% to about 80%, alternatively from about 45% to about 75%, alternatively from about 50% to about 70%, alternatively from about 50% to about 60%, alternatively from about 45% to about 55%, alternatively from about 55% to about 65%, alternatively from about 65% to about 75%, alternatively combinations thereof, of a total water content.

Free of Abrasives

Preferably, the oral care composition of the present invention is substantially free of abrasives. The term "abrasive", for the purpose of present invention, includes calcium-containing abrasives and silica abrasives. The calcium-containing abrasives may be selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In one embodiment where the calcium-containing abrasive is calcium carbonate, the calcium carbonate can be selected from the group consisting of fine ground natural chalk, ground calcium carbonate, precipitated calcium carbonate, and combinations thereof. The silica abrasives may generally have an average particle size ranging from 0.1 to 30 μm, and preferably from 5 to 15 μm. The silica abrasives can be precipitated silica or silica gels such as the silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129.

Preferably, the oral care composition of the present invention contains low levels of abrasives. For example, the oral care composition may comprise from 0% to about 5% by weight of the composition, of abrasives, alternatively from 0% to about 3%, alternatively from 0% to 2%, alternatively from 0% to about 1%, alternatively less than about 3%, or less than about 2%, or less than about 1%, or less than about 0.5%, by weight of the composition. Preferably, the composition is essentially free of the abrasives, more preferably free of the abrasives.

Humectants

The oral care compositions herein may contain humectants. The humectants serve to keep the oral care composition from hardening upon exposure to air, to give a moist feel to the mouth, and, for particular humectants, to impart a desirable sweetness of flavor.

Suitable humectants for the present invention include edible polyhydric alcohols such as glycerin, sorbitol, xylitol, erythritol, butylene glycol, polyethylene glycol, propylene glycol, and combinations thereof. In one embodiment, the humectant is selected from sorbitol, glycerin, and combinations thereof. In another embodiment, the humectant is glycerin. In yet another embodiment, the humectant is sorbitol. In one embodiment, the oral care composition comprises from about 1% to less than about 50% of humectants by weight of the composition, preferably from about 10% to about 40%. In yet another embodiment, the oral care composition contains from about 15% to about 30% of glycerin by weight of the oral care composition.

In one example, the oral care composition of the present invention is substantially free of ethanol, preferably essentially free of ethanol. The ethanol is not desirable, in some cases, as it may cause irritating feeling to the users.

Flavorant

The oral care compositions herein may include from about 0.001% to about 5%, alternatively from about 0.01% to about 4%, alternatively from about 0.1% to about 3%, alternatively from about 0.5% to about 2%, alternatively combination thereof, of a flavorant composition by weight of the oral care composition. The term flavorant composition is used in the broadest sense to include flavor ingredients, or sensates, or sensate agents, or combinations thereof. Flavor ingredients may include those described in U.S. Publication No. 2012/0082630A1 at paragraph 39; and sensates and sensate ingredients may include those described at paragraphs 40-45, incorporated herein by reference.

Examples of flavor compositions or flavor ingredients include: mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta-damascenone, ionone, gamma-decalactone, gamma-nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

Sensates such as cooling, warming, and tingling agents are useful to deliver signals to the users. The most well-known cooling agent is menthol, particularly 1-menthol, which is found naturally in peppermint oil. Among synthetic cooling agents, many are derivatives of or are structurally related to menthol, i.e., containing the cyclohexane moiety, and derivatized with functional groups including carboxamide, ketal, ester, ether and alcohol. Examples include the p-menthanecarboxamide compounds such as N-ethyl-p-menthan-3-carboxamide (known commercially as "WS-3"). An example of a synthetic carboxamide cooling agent that is structurally unrelated to menthol is N,2,3-trimethyl-2-isopropylbutanamide. Additional exemplary synthetic cooling agents include alcohol derivatives such as 3-1-menthoxypropane-1,2-diol, isopulegol, p-menthane-3,8-diol; menthone glycerine acetal (known commercially as "MGA"); menthyl esters such as menthyl acetate, menthyl acetoacetate, menthyl lactate, and monomenthyl succinate.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl-2-(1-pyrrolidinyl)-2-cyclopenten-1-one (5-MPC); 2,5-dimethyl-4-(1-pyrrolidinyl)-3(2H)-furanone (DMPF); icilin (also known as AG-3-5, chemical name 142-hydroxyphenyll-4-[2-nitrophenyl]-1,2,3,6-tetrahydropyrimidine-2-one).

Some examples of warming agents include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Examples of some tingling agents include capsaicin; homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof.

The oral care compositions herein can further include herbal ingredients such as extracts of chamomile, oak bark, melissa, rosemary and *salvia*. These, and some of the herb-derived flavoring components can be included at levels just sufficient to provide a contribution to the flavor or they can be added at higher levels, such as 1% or more, in order to provide a greater therapeutic effect.

Preservatives

The oral care composition of the present invention may comprise preservatives. The preservatives may be benzyl alcohol, phenoxyethanol, sorbitan caprylate (Velsan SC®), 1-2 hexanediol & caprylyl glycol (Symdiol 68®), parabens and or combinations. The paraben may comprise methyl paraben or propyl paraben or combination thereof. Levels of benzyl alcohol or phenoxyethanol may be present at the amount of from greater than about 0.10% to about 0.40%, preferably about 0.15% to about 0.30%, more preferably about 0.17% to about 0.23%, alternatively from about 0.18% to about 0.22%, alternatively from about 0.19% to about 0.21%, alternatively about 0.20%, by weight of the composition. The levels of Velsan C® maybe present at the amount of from about 0.10% to about 0.50%, preferably from about 0.20% to about 0.40%, more preferably alternatively from about 0.25% to about 0.30%. The level of Symdiol 68® maybe present from about 0.10% to about 0.80%, preferably from about 0.10% to about 0.50% and more preferably from about 0.20% to about 0.30%. Levels of paraben may be present at the amount of from about 0.01% to about 0.11%, preferably from about 0.02% to about 0.10%, more preferably from about 0.03% to about 0.09%, by weight of the composition. In one embodiment, the composition comprises from about 0.005% to about 0.1%, preferably from about 0.01% to about 0.08%, alternatively from about 0.01% to about 0.05%, of propyl paraben by weight of the composition. In another embodiment, the composition comprises from about 0.01% to about 0.1%, preferably from about 0.02% to about 0.07%, alternatively from about 0.03% to about 0.05%, of methyl paraben by weight of the composition.

In yet another embodiment, the paraben comprises a combination of methyl paraben and propyl paraben, wherein there is a greater weight ratio of methyl paraben to propyl paraben. In yet still another embodiment, the paraben is methyl paraben and propyl paraben, wherein the weight ratio of methyl paraben to propyl paraben is from about 5:3 to about 30:3, preferably greater than about 5:3 to about 20:3, more preferably from about 6:3 to about 15:3.

In one embodiment, the oral care compositions of the present invention are substantially free of triclosan (i.e., 5-chloro-2-(2,4-dichlorophenoxy)phenol), preferably free of triclosan.

Sweetener

The oral care compositions herein may include a sweetening agent. These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Sweetening agents are generally used in oral care compositions at levels of from about 0.005% to about 5%, alternatively from about 0.01% to about 1%, by weight of the composition, alternatively from about 0.1% to about 0.5%, alternatively combinations thereof.

Coloring Agents

The oral care compositions herein may include a coloring agent (i.e., pigments, dyes and opacifiers). The coloring agent may be in the form of an aqueous solution, preferably 1% coloring agent in a solution of water. Titanium dioxide may also be added to the present oral care composition. Titanium dioxide is a white powder which adds opacity to the oral care compositions. Titanium dioxide generally comprises from about 0.25% to about 5%, by weight of the composition. It will be appreciated that selected components for the compositions must be chemically and physically compatible with one another.

Anti-Calculus Agent

The oral care compositions may include an effective amount of an anti-calculus agent, which in one embodiment may be present from about 0.05% to about 50%, alternatively from about 0.75% to about 25%, alternatively from about 0.1% to about 15%. Non-limiting examples include those described in U.S. Publication No. 2011/0104081A1 at paragraph 64, and those described in U.S. Publication No. 2012/0014883A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably from about 0.01% to about 2%, more preferably from about 0.1% to about 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

Other Ingredients

The present oral care composition may comprise other oral care active. For example, the oral care composition may comprise vitamins selected from Vitamin C, Vitamin E, Vitamin B5, and the combinations thereof. Herein the term "Vitamin" means said vitamins and all derivatives thereof. The ingredients may provide additional benefits to the oral care composition. The use of extracellular antioxidants, e.g. ascorbate or α-tocopherol, as chain breaking or radical scavenging antioxidants, helps control and modulate the intracellular reactive oxygen species (ROS) that can cause host-tissue damage. The use of dexpanthenol can improve epithelialization and induce the proliferation phase in the wound healing of damaged tissue.

In some embodiments, the oral care composition may comprise from about 0.1% to about 10%, preferably from about 0.5% to about 8%, or from about 0.5% to about 5%, by weight of the composition, of vitamins selected from Vitamin C, Vitamin E, Vitamin B5, or the combinations thereof. The vitamins described in the present invention means said vitamins and all derivatives thereof.

The present oral care composition may further comprise the usual and conventional ancillary components such as surfactants, anti-microbial agents, fluoride ions, and other ingredients that are known to one skilled in the art. It will be appreciated that selected components for the oral care compositions must be chemically and physically compatible with one another.

Method of Use

The present invention also relates to methods for treating the oral cavity comprising applying to the intraoral tissue (e.g. oral mucosa, gingiva) of the oral cavity of a subject, particularly the gum tissue, leaving on for more than 2 minute, preferably more than 10 minutes, more preferably more than 30 minutes, or more than 60 minutes or longer. The method of use herein comprises contacting a subject's oral mucosa (e.g. gingival margin or gingival sulcus/pockets) with the oral care composition according to the present invention.

The present invention further relates to a method of improving Gum Health of a subject using the oral care composition described herein comprising the step of applying the oral care composition onto the intraoral tissue of a subject, preferably applying along the gingival margin or sulcus at least once a day, preferably at least twice a day, more preferably every time immediately after brushing teeth. The term "immediately" herein means within 1 hour, preferably within 30 minutes, more preferably within 15 minutes, alternatively within 10 minutes. Preferably, the oral care composition can be applied onto the intraoral tissue of a subject by using an applicator, which applicator has a handle and a head, to spread the oral care composition along the gingival margin or sulcus of the subject. Preferably, the oral care composition is applied on the head of the applicator before being applied onto the intraoral tissue.

The present invention further relates to a method of improving Gum Health of a subject, comprising at least two steps: (a) brushing teeth with an antibacterial toothpaste, preferably a stannous containing toothpaste, and immediately followed by (b) applying the oral are composition as defined herein onto the intraoral tissue of the subject, preferably applying along the gingival margin, sulcus or pockets.

Test Methods

Test 1: Rheological Test Method

A Rheological Test Method is described for assessing viscosity profile (and ran according to manufacturing instructions). The viscosity profiles are tested on a TA AR2000 rheometer (available from TA Instruments, New Castle, United States) by using Dentifrice Macro Rheology Test procedure. The geometry used is 40 mm steel parallel plate with solvent trap. Dentifrice is placed on the Peltier Plate of AR2000 rheometer and the Gap setting is 1000 micron. Dentifrice Macro Rheology Test consists of stress sweep oscillation, frequency sweep oscillation and steady state flow tests. The key parameter settings are listed: (a) Stress sweep step: Oscillation Stress (Pa): 0.01-500; (b) Frequency (Hz): 1.0; (c) Frequency sweep step: Frequency (Hz): 0.1-10, and Controlled Oscillation Stress (Pa): 1.5; (d) Steady state flow step 1: Shear rate ($s^{-1}$): 0.01-100; and (e) Steady state flow step 2: Shear rate ($s^{-1}$): 100-0.01.

Shear flow test is a viscosity testing mode to measure the viscosity at different shear rates. Steady state flow test is a flow in which the velocity at every point does not vary with time. The three main parameters in this test are viscosity, shear rate and shear stress. Power Law Model is a well-known model used to characterize the relationship between viscosity or shear stress and shear rate over the range of shear rates where shear thinning occurs in a Non-Newtonian fluid. It quantifies overall viscosity range and degree of deviation from Newtonian behavior. The Power Law Model is described as $\eta = K \gamma^{n-1}$, wherein $\eta$=viscosity and $\gamma$=shear rate. K is known as the Viscosity Consistency Coefficient, describing the overall range of viscosities across the part of the flow curve that is being modelled. The exponent "n" is known as the rate index. K and $\eta$ can be determined by Power Law Model fitting. Based upon rate index n, the Power Law Model describes three basic types of flow:

n=1 Newtonian behavior
n<1 Shear thinning (or Pseudoplastic)
n>1 Shear thickening The viscosity profiles of the composition herein are represented by the Viscosity Consistency Coefficient K (Pa·s) determined by Power Law Model fitting with the shear rate range of 0.1-10 $s^{-1}$.

Test 2: Mucoadhesion Test Method

Mucoadhesion Test Method is provided. Test samples are labeled with Fluorescein isothiocyanate (FITC) at room temperature for 1 hour. The resulting solutions are dialyzed in phosphate buffered saline (PBS) for 48 h in order to remove the free FITC molecules. The silica wafers are treated with a mixture of ethanol/(3-Aminopropyl)triethoxysilane (APTES)/ammonia solution (20:4:1, v/v/v) for 8 hours and are then rinsed with ethanol and water, and dried to obtain the amine-functionalized silica wafers ($NH_2$—SW). $NH_2$—SW are incubated in mucin solution for 8 hours at room temperature. The mucin modified silica wafers are incubated with test sample in a PBS buffer in a shaker at 37° C. for 12 hours followed by rinsing with deionized water. The fluorescence images of the mucin modified silica wafers are taken by a fluorescence microscopy, and used for measurement of Fluorescent Intensity (H) in ImageJ software (National Institutes of Health, USA, (https://imagej.nih.gov/ij/)). The Fluorescent Intensity Percentage ("FI %"), which is used to describe the "Mucoadhesion Index", is the fluorescent pixels relative to total pixels in a normalized image field. Therefore, a first test sample having a higher FI % has stronger mucoadhesion compared to a second test sample having a lower FI %.

Test 3: Adhesiveness Test Method

The adhesiveness of samples is tested using Texture Analyser (TA Plus/30), Stable Micro System (Surrey, UK). The procedure is described as below:

1. Sample preparation: pipe out of gel or ointment sample from package as the amount of '0.03±0.005 g' to the test plate.
2. Make TA sequence to enable the instrument action: the probe is compressed into each sample, follow the determined programmed sequence (speed of 10 mm/sec, force of 5 g for stage 2; speed of 1mm/sec, Force of 200 g for stage 4, and time is 1 sec for stage 5).
3. Instrument & accessory setting:
   3.1 Try the test with available probe options: metal round plate
   3.2 TA setting as 'compression'
4. All analyses should be performed on 5 replicates.
5. measurement: Adhesiveness: the work necessary to overcome the attractive forces between the surface of the sample and the surface of the probe.
6. Data calculation: Leverage programmed TTA data analysis macro (e.g. Force 5 g).

The adhesiveness values (unit: gf*sec) describes the energy necessary to overcome the attractive forces between the surface of the sample and the surface of the probe.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Example 1: Examples A and B

Examples A and B are leave-on oral care gel compositions shown in Table 1 below with amounts of components described as a weight percentage ("wt %"). These examples are prepared by conventional methods. Example A is a comparative gel composition containing sodium hyaluronate (as a source of hyaluronic acid) but without trehalose. Example B is an inventive gel composition containing sodium hyaluronate and 10 wt % of trehalose.

TABLE 1

Examples A to B -- Gel Compositions

| Ingredients | Amount (Wt %) | |
| --- | --- | --- |
| | Comparative Example A | Inventive Example B |
| Glycerin | 20 | 20 |
| Propyl Paraben | 0.03 | 0.03 |
| Xylitol | 2 | 2 |

TABLE 1-continued

Examples A to B -- Gel Compositions

| | Amount (Wt %) | |
|---|---|---|
| Ingredients | Comparative Example A | Inventive Example B |
| Sodium Saccharin | 0.1 | 0.1 |
| Sodium Hydroxide (50 wt %) | 0.9 | 0.9 |
| PEG 300 | 0.5 | 0.5 |
| Carbomer | 1.5 | 1.5 |
| PVPK90 | 1.5 | 1.5 |
| Sodium Hyaluronate | 0.526 | 0.526 |
| Trehalose | 0 | 10 |
| Panthenol (powder) | 0.5 | 0.5 |
| Tocopherol Acetate | 0.5 | 0.5 |
| Sodium Ascorbyl Phosphate | 0.91 | 0.91 |
| Sodium Pyrophosphate | 0.5 | 0.5 |
| Preservatives | 0.15 | 0.15 |
| Flavorant | 1.03 | 1.03 |
| Water & Minors (e.g. Coloring Agent.) | Q.S. | Q.S. |
| Total | 100 | 100 |

*Sodium hyaluronate having weight average molecular weight of ~1,400,000 Da.

Example 2: Barrier Protection Test

Barrier Protection Test is described here. This test assesses the barrier protection ability of a leave-on oral care composition by using capsaicin to treat a cell covered by the sample.

Cell Culture:

Human gingival epithelial (HGE) cell is maintained in a 37° C. incubator with 5% $CO_2$ saturation. Adding 10 wt % fetal calf serum, and 1 wt % penicillin-streptomycin to Dulbecco's Modified Eagle's Medium (DMEM, Gibco) to make the complete culture medium for these cells, which is changed every 2-3 days.

Barrier Protection Analysis by Real Time Cell Analyzer (RTCA):

The real time cell analyzer (RTCA) xCELLigence RTCA DP (ACEA Bioscience Inc., San Diego, CA) equipment, based on impedance measurement, is used to monitor the barrier protection of sample. 50 ul of the complete culture medium is added to E-plates to obtain background readings, followed by the addition of 100 ul of the cell suspension. The E-plates containing 28000 cell/well are incubated at 37° C., 5% $CO_2$ for 22-24 h until cells are confluent. The culture medium is changed to DMEM or DMEM with 50 times diluted sample (sample information is as Table 2 below) and is incubated at 37° C., 5% $CO_2$ for 2 h. The barrier disruptor (capsaicin to a final concentration of 75 uM in this case) is added to wells of the E-plate. Impedance is reflected as a Cell Index ("CI") and recorded continuously for 16-24 hs, and reported as a CI curve.

TABLE 2

Sample Information:

| Sample Name | Details | HA (Wt %) | Trehalose (Wt %) | Preservative System | Polymer System |
|---|---|---|---|---|---|
| C (Control) | Trehalose Solution | — | 10 | — | — |
| D (Comparative) | Example A | 0.5 | — | same amount | |
| E (Inventive) | Example B | 0.5 | 10 | | |

The CI curve is normalized at the time point just before adding samples. The normalized CI at 3 h, after adding the barrier disruptor, is compared to blank control are recorded. The barrier protection percentage is calculated by the below formulation.

Barrier Protection Percentage=(normalized CI of sample−normalized CI of capsaicin)/normalized CI of blank.

TABLE 3

Barrier Protection Results

| Sample (Diluted) | Barrier Protection Percentage |
|---|---|
| Control Capsaicin (75 uM) | 0% |
| C (Control) | 0% |
| D (Comparative) | 22% |
| E (Inventive) | 67% |

The results in Table 3 shows that Sample C (i.e., a trehalose only control with a final concentration of 0.2 wt %) does not show any barrier protection compared to the Control Capsaicin (i.e., barrier disruptor). Sample D (i.e., comparative Example A which contains hyaluronic acid but without trehalose) exhibits some level of barrier protection at 22%. Notably, Sample E (i.e., inventive Example B), which contains both hyaluronic acid and trehalose, exhibits a significant barrier protection at 67% that is over three fold higher than Sample D. These results show the significantly incremental barrier protection by those leave-on oral care compositions combining hyaluronic acid and gum-strengthening polyol such as trehalose.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   a) from about 30% to about 85%, by weight of the composition, of total water content;
   b) from about 0.01% to about 10%, by weight of the composition, of a hyaluronic acid or a salt thereof; and c) from about 0.5% to about 20%, by weight of the composition, of a gum-strengthening polyol, wherein the gum-strengthening polyol comprises trehalose;

wherein the oral care composition is substantially free of abrasives; and wherein the oral care composition is a leave-on composition.

2. The oral care composition according to claim 1, wherein the gum-strengthening polyol further comprises rafiose, stachyose, verbascose, isomalt, maltitol, lactitol, maltotriitol, maltotetraitol, polyglycitol, or combinations thereof.

3. The oral care composition according to claim 2, wherein the gum-strengthening polyol further comprises isomalt.

4. The oral care composition according to claim 1, further comprising from about 0.1% to about 10%, by weight of the composition, of a polyacrylic acid.

5. The oral care composition according to claim 1, wherein the hyaluronic acid has a weight average molecular weight of from about 900,000 Daltons to about 5,000,000 Daltons.

6. The oral care composition according to claim 1, further comprising an additional polymer selected from the group consisting of xanthan gum, carrageenan, carboxymethyl cellulose, hydroxyethyl cellulose, hydroxypropyl cellulose, hydroxymethyl cellulose, hydroxypropyl cellulose, hydroxymethyl cellulose, polyvinyl pyrrolidine, co-polymers of maleic anhydride with methyl vinyl ether having a weight average molecular weight of about 30,000 Daltons to about 1,000,000 Daltons, and combinations thereof.

7. The oral care composition according to claim 1, wherein the total water content is from about 40% to about 80%, by weight of the composition.

8. The oral care composition according to claim 1, further comprising a humectant selected from the group consisting of glycerin, sorbitol, xylitol, erythritol, butylene glycol, polyethylene glycol, propylene glycol, and combinations thereof.

9. The oral care composition according to claim 1, wherein the oral care composition is substantially free of ethanol.

10. The oral care composition according to claim 1, further comprising a vitamin selected from the group consisting of Vitamin C, Vitamin E, Vitamin B5, and combinations thereof.

11. A method of improving Gum Health of a subject, the method comprising the steps of applying the oral care composition of claim 1 onto intraoral tissue of the subject, and leaving the oral care composition on the intraoral tissue for a duration of time of from about 1 minute to about 1000 minutes; and optionally wherein the applying step is conducted as the last step of an oral hygiene regimen.

12. The method of claim 11, wherein the oral care composition is applied onto the intraoral tissue of the subject with an applicator comprising a handle and a head to spread the oral care composition onto the intraoral tissue of the subject.

13. A method of improving Gum Health of a subject, the method comprising the steps of:
(a) brushing teeth of the subject with an antibacterial toothpaste; and
(b) subsequently, applying the oral care composition of claim 1 onto intraoral tissue of the subject, and leaving the oral care composition on the intraoral tissue for a duration of time of at least about 2 minutes.

14. The method of claim 13, wherein the oral care composition is applied onto the intraoral tissue of the subject with an applicator comprising a handle and a head to spread the oral care composition onto the intraoral tissue of the subject.

15. A kit comprising a toothpaste and the oral care composition according to claim 1.

16. A kit comprising the oral care composition according to claim 1 and a delivery carrier, wherein the delivery carrier comprises strip, film of material, dental tray, aligner, sponge material, applicator, or mixtures thereof.

17. The oral care composition according to claim 1, wherein the gum-strengthening polyol is present in the amount of about 0.5% to about 18%, by weight of the composition.

18. The oral care composition according to claim 1, wherein the hyaluronic acid is present in the amount of from about 0.1% to about 5.0%, by weight of the composition.

19. The oral care composition according to claim 6, wherein the additional polymer is present in the amount of from about 0.1% to about 10%, by weight of the composition.

20. The oral care composition according to claim 8, wherein the humectant is present in the amount of from about 1% to about 50%, by weight of the composition.

\* \* \* \* \*